(12) United States Patent
Bala et al.

(10) Patent No.: US 11,544,424 B2
(45) Date of Patent: Jan. 3, 2023

(54) METHOD AND SYSTEM FOR CREATING A CUT MASK FROM A 3D SURFACE MESH

(71) Applicant: Palo Alto Research Center Incorporated, Palo Alto, CA (US)

(72) Inventors: Raja Bala, Pittsford, NY (US); Vijay Kumar Baikampady Gopalkrishna, San Jose, CA (US); Chaman Singh Verma, Mountain View, CA (US); Scott K. Stanley, Mason, OH (US); Andrew P. Rapach, Liberty Township, OH (US)

(73) Assignee: Palo Alto Research Center Incorporated, Palo Alto, CA (US)

(*) Notice: Subject to any disclaimer, the term of this patent is extended or adjusted under 35 U.S.C. 154(b) by 1040 days.

(21) Appl. No.: 16/237,386

(22) Filed: Dec. 31, 2018

(65) Prior Publication Data

US 2020/0210540 A1 Jul. 2, 2020

(51) Int. Cl.
*G06F 30/20* (2020.01)
*A45D 44/00* (2006.01)
(Continued)

(52) U.S. Cl.
CPC .......... *G06F 30/20* (2020.01); *A45D 44/002* (2013.01); *A61K 8/0212* (2013.01);
(Continued)

(58) Field of Classification Search
CPC ....... G06T 19/20; G06T 17/205; G06T 19/00; G06T 2219/2021; G06T 17/20; G06T 17/00; G06T 2200/08; G06T 2219/008; A61K 8/0212; G06F 30/20; A45D 44/002; A61M 2207/00; A61M 2207/10; A62B 18/02; G06V 10/225; G06V 10/46; G06V 10/471
See application file for complete search history.

(56) References Cited

U.S. PATENT DOCUMENTS 9,799,096 B1 * 10/2017 De la Torre .......... A63F 13/655
2015/0123967 A1 * 5/2015 Quinn ...................... G06T 7/60
345/419

(Continued)

FOREIGN PATENT DOCUMENTS

WO 2018002915 A1 1/2018

*Primary Examiner* — Xilin Guo
(74) *Attorney, Agent, or Firm* — Shun Yao; Yao Legal Services, Inc.

(57) ABSTRACT

A system is provided for generating a custom article to fit a target surface. During operation, the system compares an input dataset with a number of cut template cut meshes. A respective cut template cut mesh includes one or more cutting paths that correspond to a boundary of the mesh. Next, the system identifies a template cut mesh that produces a closest match with the input dataset, and applies global geometric transformations to the identified template cut mesh to warp the template cut mesh to conform to the input dataset. The system further refines and projects a set of boundary and landmark points from the template cut mesh to the input dataset to define cutting paths for the input dataset. Next, the system applies cutting paths to the input dataset to produce a cut-and-trimmed mesh.

20 Claims, 7 Drawing Sheets
(5 of 7 Drawing Sheet(s) Filed in Color)

(51) Int. Cl.
  *A61K 8/02* (2006.01)
  *G06T 17/20* (2006.01)
  *G06T 19/20* (2011.01)
  *G06T 19/00* (2011.01)
  *A62B 18/02* (2006.01)

(52) U.S. Cl.
  CPC ............ *G06T 17/205* (2013.01); *G06T 19/00* (2013.01); *G06T 19/20* (2013.01); *A61M 2207/00* (2013.01); *A61M 2207/10* (2013.01); *A62B 18/02* (2013.01); *G06T 2219/2021* (2013.01)

(56) References Cited

U.S. PATENT DOCUMENTS

| | | | |
|---|---|---|---|
| 2017/0256093 A1* | 9/2017 | Choi | G06T 19/20 |
| 2018/0043122 A1 | 2/2018 | Oenning et al. | |
| 2018/0157901 A1* | 6/2018 | Arbatman | H04L 51/10 |
| 2020/0046226 A1* | 2/2020 | Stanley | G06F 30/20 |

\* cited by examiner

METHOD AND SYSTEM FOR CREATING A CUT MASK FROM A 3D SURFACE MESH

BACKGROUND

Field

This disclosure is generally related to the field of creation of 3D masks. More specifically, this disclosure is related to a method and system for creating a cut mask from a 3D surface.

Related Art

The recent development of 3D manufacturing technologies has created a number of new applications and products. For example, it is now possible to generate personalized face masks, the interior surface of which contains an application of skincare products. When such a mask is worn, the product comes in direct contact with the facial skin, thus providing a highly effective treatment.

Although the process of creating 3D masks often involves using computer graphics technologies with 3D scanned images, these processes nevertheless often require human input and manipulation, and therefore can be laborious and incur high costs. Therefore, it is beneficial to reduce the amount of human input and intervention in the creation of 3D masks.

SUMMARY

Embodiments described herein provide a system for generating a custom article to fit a target surface. This system can be a digital tool for defining cut paths. During operation, the system receives an input dataset that represents a 3D input mesh of the target surface. This input dataset can be the scan data of the target surface. The system then compares the input dataset with one or more cut template meshes (also referred to as template cut paths, template meshes, template masks, or templates), wherein a respective cut template mesh includes one or more cutting paths that corresponds to a desired boundary or perimeter of the custom article and optionally one or more openings corresponding to desired openings in the custom article. Next, the system identifies a template mesh that produces a closest match with the input dataset. The system subsequently applies a global geometric transformation to the identified template mesh to warp the template mesh to conform to the input mesh from the input dataset. The system further refines and projects a set of boundary and landmark points from the template mesh to the input dataset to define one or more cutting paths for the input dataset. Next, the system applies the defined one or more cutting paths to the input dataset to produce a cut-and-trimmed mesh, and produces the custom article based on the cut-and-trimmed mesh.

In a variation on this embodiment, the target surface is a portion of a human body.

In a further variation, the target surface is a human face.

In a variation on this embodiment, the custom article is a face mask.

In a further variation, while producing the custom article based on the cut-and-trimmed mesh, the system can use laser, scissors, or other subtractive manufacturing method for the custom article based on the cut-and-trimmed mesh. In a further variation, an additive approach (e.g., 3D printing) could be used for manufacturing wherein the cut and trimmed mesh is used to produce the custom applicator directly. In some embodiments, a combination of additive and subtractive methods could also be employed.

In a variation on this embodiment, the system further allows manual editing of the defined cut paths prior to producing the custom article.

In a variation on this embodiment, the system further determines that there is sufficient difference between the final cut-and-trimmed mesh and the present library of template meshes, and adds the cut-and-trimmed mesh to a library of template meshes.

In a variation on this embodiment, while identifying the template mesh that produces the closest match with the input dataset, the system performs a global affine transformation between a respective template mesh and the input dataset.

In a variation on this embodiment, while refining and projecting the landmark points from the template mesh to the input dataset, the system performs a locally varying affine transformation at each landmark point based on correspondence relationship between the template mesh and the input dataset as a result of the global geometric transformation.

BRIEF DESCRIPTION OF THE FIGURES

The patent or application file contains at least one drawing executed in color. Copies of this patent or patent application publication with color drawing(s) will be provided by the Office upon request and payment of the necessary fee.

In the figures, like reference numerals refer to the same figure elements.

DETAILED DESCRIPTION

The following description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the embodiments described herein are not limited to the embodiments shown, but are to be accorded the widest scope consistent with the principles and features disclosed herein.

The embodiments described herein solve the problem of automatically trimming and cutting a raw 3D mesh from scanned data to produce a cut mask that can fit on a contoured surface such as a human face. After receiving the raw data which represent a scanned 3D target surface, the system can compare it with a library of predefined template masks and identify the most similar template mask. Subsequently, the system can transfer the existing cut paths from the most similar template mask to the received input dataset 3D mesh using geometric transformations, and produce a cut mask corresponding to the received input dataset 3D mesh. The method can be used to produce any custom article for fitting onto any target surface. As a result, the process of creating 3D cut masks or machine-cut articles can benefit from improved productivity and scalability.

Currently, it is possible to generate personalized face masks whose interior contains an application of skincare products. When such a mask is worn, the product comes in direct contact with facial skin, thus providing highly effective treatment. Creation of a personalized mask is typically a multi-step process that begins with scanning a subject's face with a 3D scanner, and fusing the resulting 3D point clouds into a coherent mesh. Ideally, this 3D mesh undergoes a process which changes the input 3D mesh into a usable 3D mask. This process typically involves various steps to trim the boundary of the mesh to remove points outside of the desired target area (such as areas corresponding to regions of hair, the ears, and optionally the neck region), to smooth the boundary into a comfortable and aesthetically pleasing border perimeter, and to cut out holes for the eyes, nostrils, and mouth. This process then results in a trimmed and cut mask. The trimmed and cut mask can then be manufactured, for example, using a 3D printer, and subsequently coated with the skincare application and shipped to the consumer.

Figure 1:
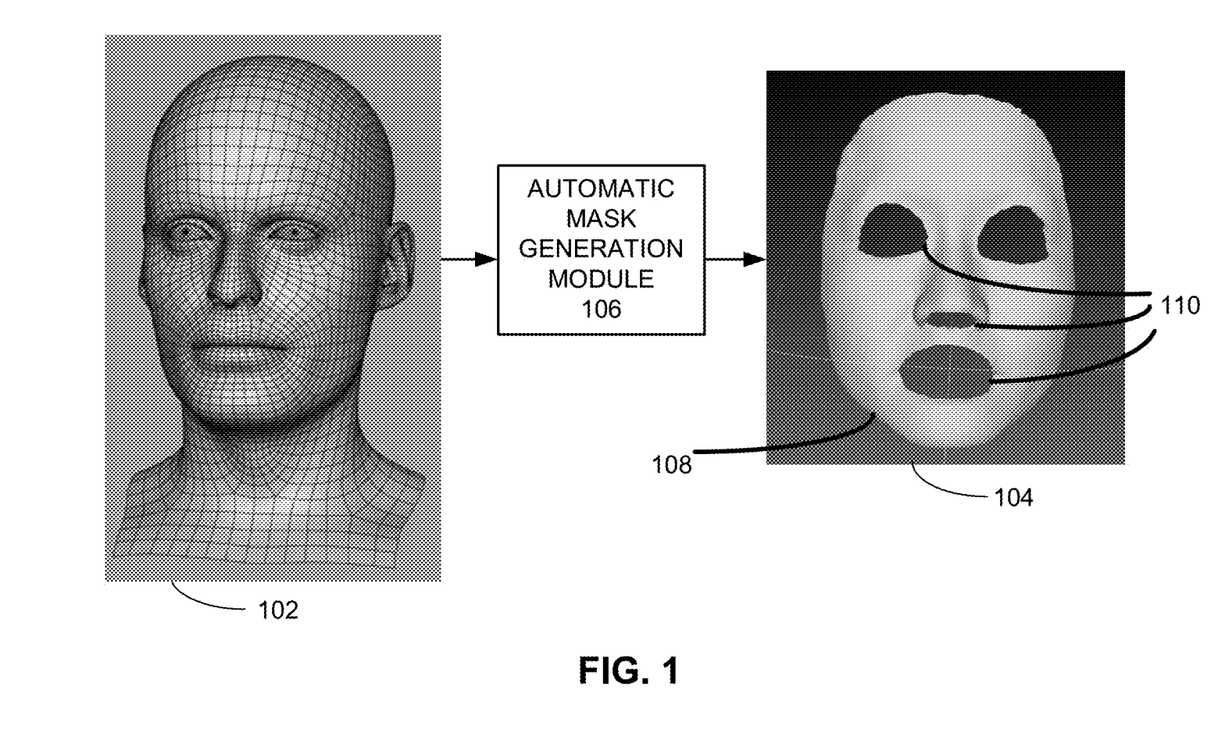
FIG. 1 illustrates an exemplary process for automatically generating a 3D mask, in accordance with an embodiment of the present application.

The process of converting a raw 3D mesh into a final cut mask is traditionally carried out by a human operator, and is thus time consuming, laborious and costly, and does not scale up economically for mass production. FIG. 1 illustrates an exemplary process for automatically generating a 3D mask, in accordance with an embodiment of the present application. A raw input 3D mesh 102, which can be represented in various data structures such as a 3D array, is input to an automatic mask generation module 106. Automatic mask generation module 106 then performs a number of processes on input 3D mesh 102 to produce a trimmed and cut 3D mask 104, as will be described in more detail later. Trimmed and cut 3D mask 104 can include landmark cutouts 110, which can include cutouts for eyes, nostrils, and mouth, and a trimmed boundary 108.

Figure 2:
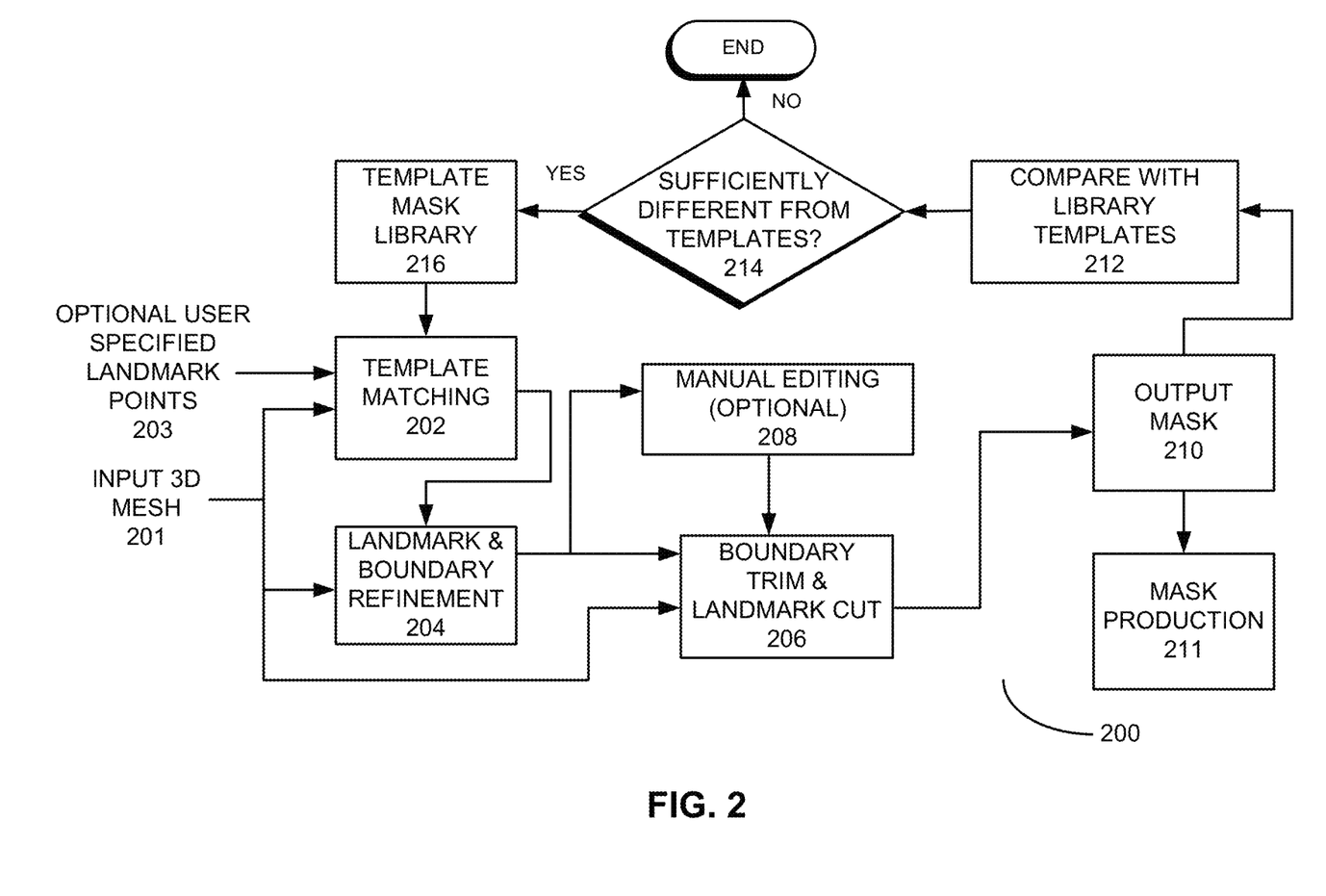
FIG. 2 illustrates an exemplary system for automatically generating 3D masks, in accordance with one embodiment of the present invention.
Figure 3:
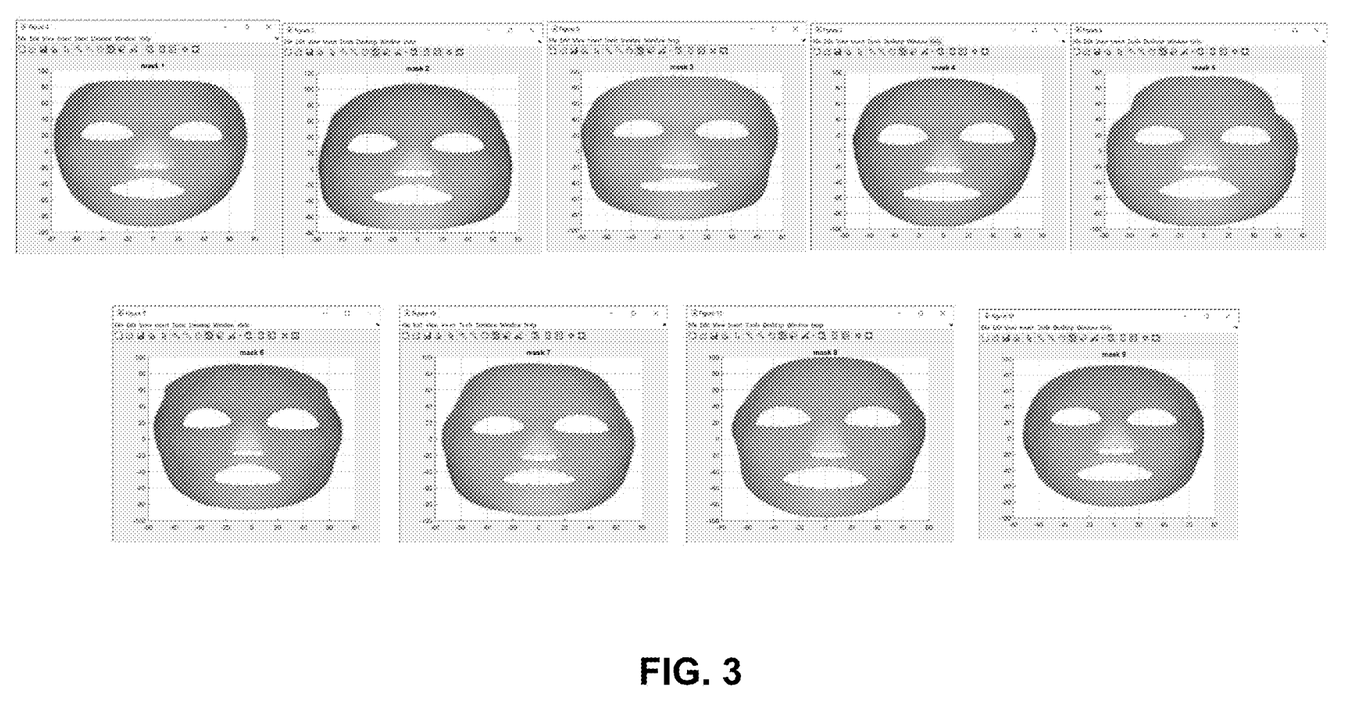
FIG. 3 shows an exemplary library of nine front-view template masks of women with different ethnic and age profiles is shown, in accordance with one embodiment of the present invention.

FIG. 2 illustrates an exemplary system for automatically generating 3D masks, in accordance with one embodiment of the present invention. In this example, an automatic 3D mask generation system 200 can include a template mask library 216, a template matching module 202, a landmark and boundary refinement module 204, a boundary trim and landmark cut module 206, an optional manual editing module 208, and a library template comparison module 212. Template mask library 216 stores one or more pre-defined template meshes (which in this case can be template masks). These template meshes, or template masks, can be a priori trimmed, cut, and pre-annotated with a set of landmark points along the exterior boundary and interior cut-outs as shown in FIG. 3.

During operation, template matching module 202 compares an input 3D face mesh 201 against the template masks in template mask library 216. Optionally, template matching module 202 also takes as input user specified landmark points 203 which identify certain landmark points on input 3D mesh 201. As a result, template matching module 202 can identify a template mask that is the closest match to input 3D mesh 201.

Subsequently, landmark and boundary refinement module 204 takes as its input the closest-matching template mask, and warps this template mask and its associated landmark and boundary points to produce an optimized fit to input 3D mesh 201. This warping process can be done via a series of geometric transforms. The warped landmark and boundary points are then projected onto input 3D mesh 201. As a result, landmark and boundary refinement module 204 can produce a set of "scissor paths" for cutting and trimming input 3D mesh 201.

Optionally, the scissor paths produced by landmark and boundary refinement module 204 can be fed to manual editing module 208, which allows a human operator to manually adjust the scissor paths using a graphical user interface. These scissor paths (either with or without manual editing) are then taken as input, together with input 3D mesh 201, by boundary trim and landmark cut module 206, which can produce the final output 3D mask 210. Output 3D mask 210 is then supplied to a mask production module 211, which can employ a 3D manufacturing method (such as 3D printing) or other methods to produce the physical 3D mask. In some embodiments, mask production module 211 can use laser, scissors, or other physical cutting technology to selectively remove a material for producing the mask in a subtractive process.

In some embodiments, library template comparison module 212 can compare the output 3D mask with the one or more template masks stored in template mask library 216 (step 214). If the output 3D mask is sufficiently different in its geometric properties (e.g., shape and size) from any of the template masks in the library, the output 3D mask is then added to the library and becomes another template mask.

Figure 4:
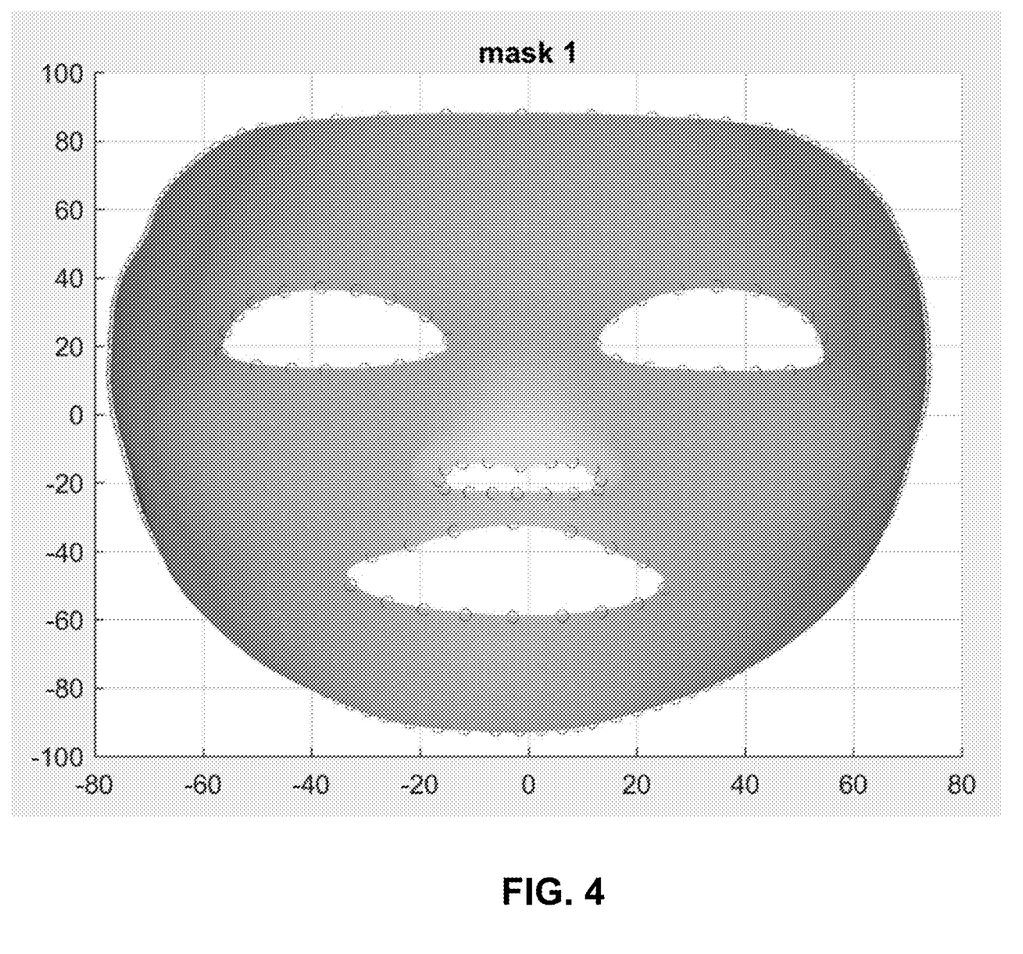
FIG. 4 shows a close-up of an exemplary template mask with pre-annotated landmark and boundary points shown in red circles, in accordance with one embodiment of the present invention.

Note that one of the goals of this system is to create a library of trimmed masks such that with high likelihood, the input mesh can be matched fairly closely to one of the template masks. In one embodiment, the template masks can be tailored for a given demographic group (e.g., age group, ethnic profile, gender, etc.), or kept as diverse as possible to ensure robustness. In some embodiments, any user data may be also input into module 202 as added step to assist with template matching such as demographic data, face shape data, skin condition, etc. FIG. 3 shows an exemplary library of nine front-view template masks of women with different ethnic and age profiles is shown, in accordance with one embodiment of the present invention. FIG. 4 shows a close-up of an exemplary template mask with pre-annotated landmark and boundary points shown in red circles, in accordance with one embodiment of the present invention.

Referring back to FIG. 2, to find the closest-matching template mask, in one embodiment, template matching module 202 can obtain the optimal global affine transform between input 3D mesh 201 and template mesh (template mask) in library 216. In one embodiment, template matching module 202 can perform an iterative closest point (ICP) matching method to derive and apply the affine transform. More details on the ICP matching method can be found in P. Besl and N. McKay, "A Method for Registration of 3-D Shapes," IEEE Trans. Pattern Analysis and Machine Intelligence, vol. 14, pp. 239-256, 1992, which is incorporated by reference herein. In a further embodiment, a user may optionally supply certain control points 203 on facial landmarks (e.g., on the eyes, nose, and mouth) on input 3D mesh, which together with the corresponding template mask's landmark points can be used to derive the affine transform. The template mask with the smallest affine fitting error is chosen as the closest match.

After the closest-matching template mask is found, template matching module 202 then applies the affine transform to this template mask and its associated landmark and boundary points. The correspondences between vertices in input 3D mesh 201 and template mask are also retained. As a result, template matching module 202 outputs a globally warped template mask.

The globally warped template with landmark and boundary points produced by template matching module 202 will likely be close to, but not coincident with input 3D mesh 201's surface. In a subsequent refinement step, landmark and boundary refinement module 204 can apply a nonlinear local warping to more accurately map the template mask's landmark and boundary points onto the correct corresponding positions on input 3D mesh 201. In one embodiment, a locally varying affine transform is derived at each landmark and boundary point using locally weighted linear regression on the point correspondences which are identified by template matching module 202. Alternatively, different methods for establishing local point correspondences may be used, e.g., matching of surface normal vectors, local curvature, or other structural and geometric properties of the 3D surface. As a final step, the warped boundary path may be projected onto input 3D mesh 201 using, for example, a polar or spherical coordinate system.

Additionally, embodiments of the present invention can employ more sophisticated methods for finding and refining the exterior face boundary in a manner that avoids noisy (e.g., hairline) regions, and holes created during the 3D scanning process. More details of such methods can be found in C. Mineo, S. G. Pierce, and R. Summan, "Novel algorithms for 3D surface point cloud boundary detection and edge reconstruction," Journal of Computational Design and Engineering, 2018, which is incorporated by reference herein. As mentioned earlier, the output of landmark and boundary refinement module 204 is a set of scissor paths on the boundaries for both exterior applicator perimeter and optionally interior cutouts for the eyes, nostrils, and mouth.

Given input 3D mesh 201 and the scissor paths found by landmark and boundary refinement module 204, boundary trim and landmark cut module 206 performs a virtual cut by eliminating all unwanted vertices and, if necessary, re-triangulating the retained vertices on input 3D mesh 201 to ensure smooth cut boundaries. Cut methods in 3D computational geometry such as flood filling can be used for this purpose. More details on these methods can be found in R. W. Noack, "A Direct Cut Approach for Overset Hole Cutting," in AIAA Computational Fluid Dynamics Conference, Miami, 2007, which is incorporated by reference herein.

Figure 5:
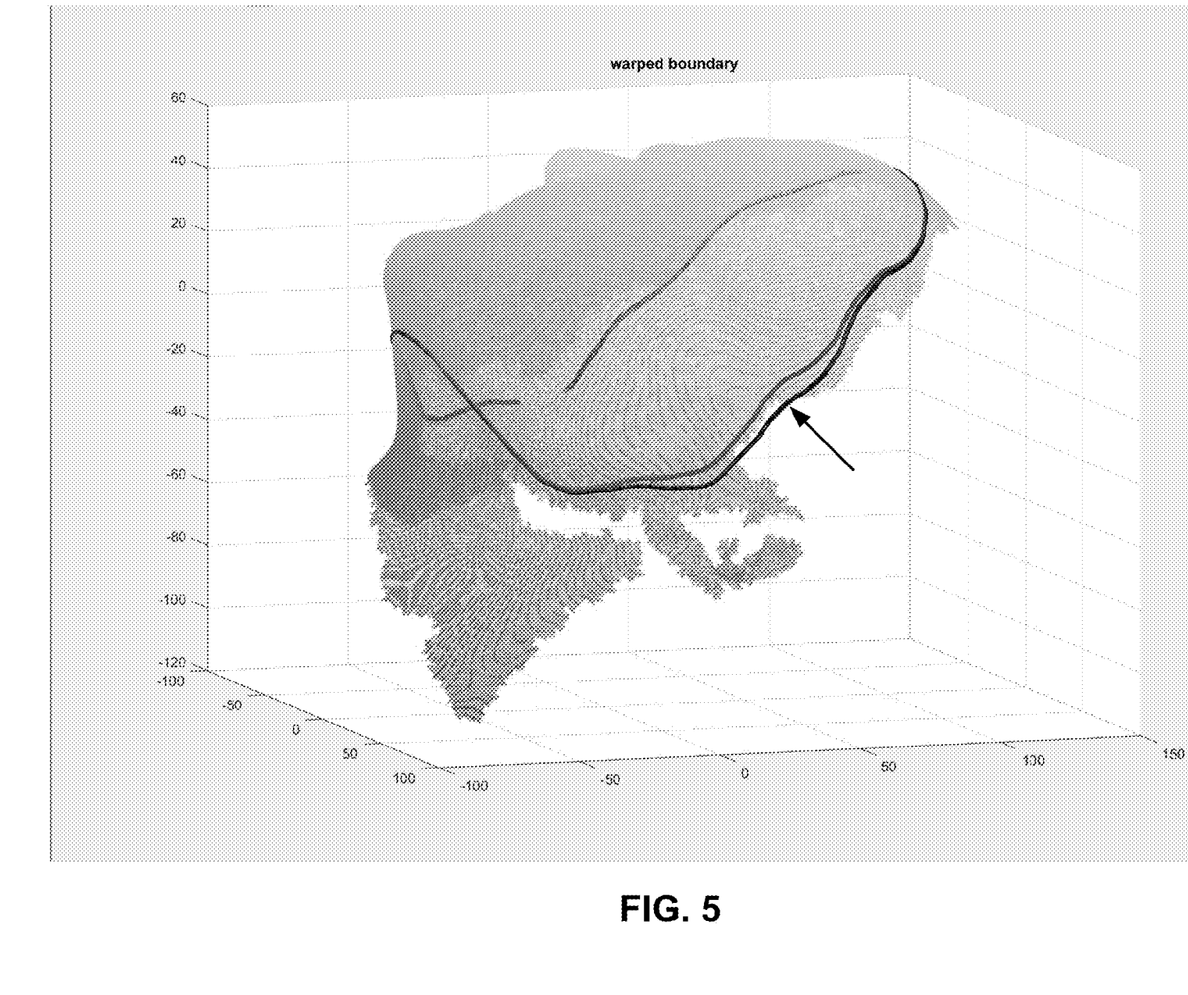
FIG. 5 shows exemplary manual editing of a cut path, in accordance with one embodiment of the present invention.

If the cut mask generated by the aforementioned steps does not produce a satisfactory result, it may be desirable for a human operator to edit and refine the mask. In one embodiment, manual editing module 208 can present the user with input mesh and boundary path in a graphical interface. The user can specify one or more points on the boundary (or landmark), and specify a target location to which that point(s) can be moved. The boundary (or landmark) is then adjusted to smoothly travel through the new target location. FIG. 5 shows exemplary manual editing of a cut path, in accordance with one embodiment of the present invention. In this example, Gaussian weighting is used to perform a smooth local warping that respects a single point shift. The black line is the original cut path, and the red line is the manually edited path. The arrow marks the location of the point that is moved in order to avoid holes (i.e., regions where there is no input data) near the input mesh boundary.

As mentioned earlier, in order to maintain a diverse and representative template mask library, output cut mask 210 can be compared against each of the template masks and added to the library if the newly cut mask is sufficiently different from all template masks. Any method for measuring template mask similarity (or difference), for example the affine fitting error method, can be used.

Figure 6:
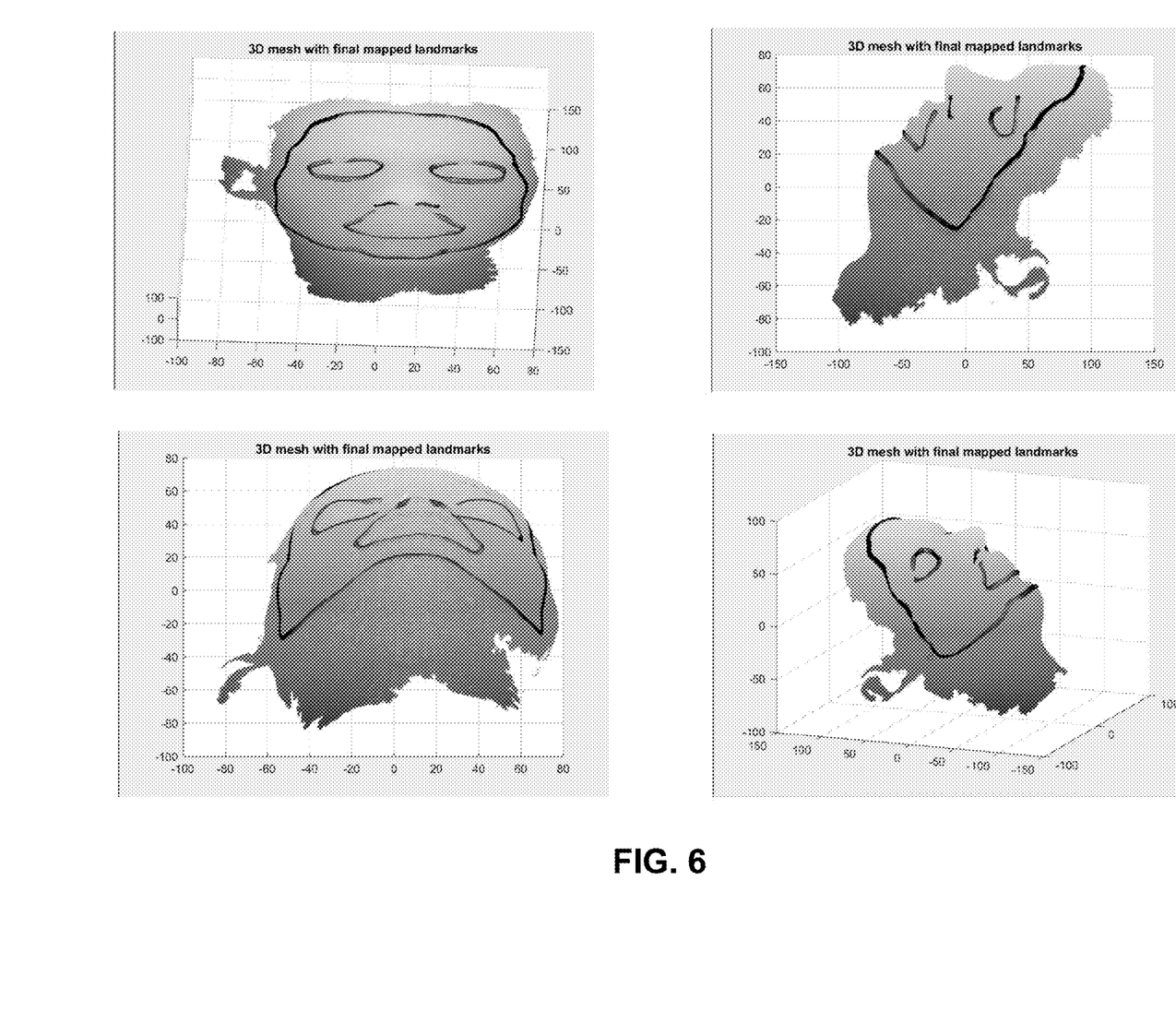
FIG. 6 shows exemplary output cut paths generated by the 3D mask generation system, overlaid on the raw input data, in accordance with one embodiment of the present invention.

FIG. 6 shows exemplary output cut paths generated by the 3D mask generation system overlaid on the raw input data, in accordance with one embodiment of the present invention.

Note that while the examples described herein are described in conjunction with face mask creation, the system can be generalized to produce any custom article for fitting onto a target 3D surface with a custom perimeter and optionally removed interior regions.

Figure 7:
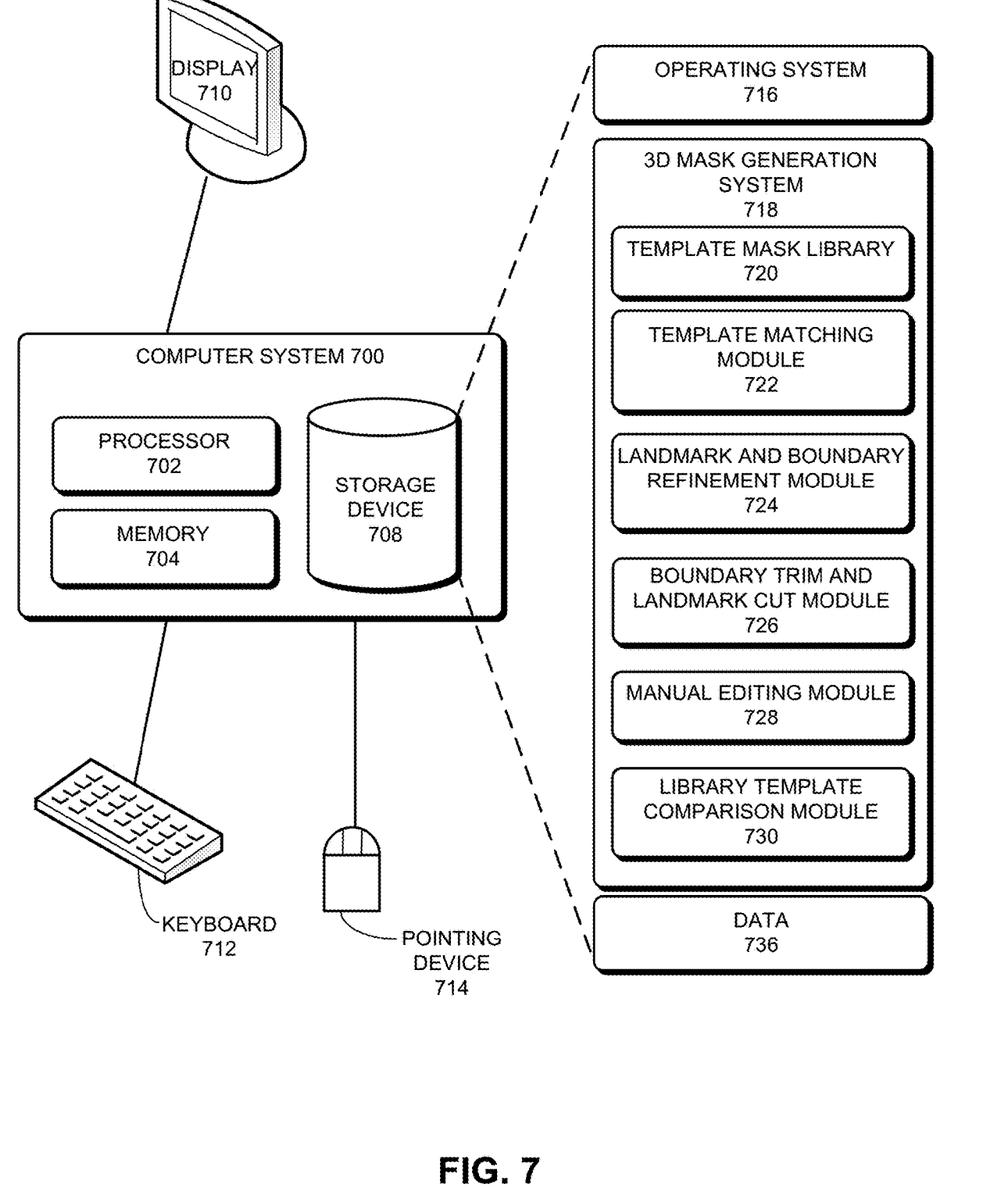
FIG. 7 illustrates an exemplary computer system that facilitates automatic generation of 3D masks, in accordance with an embodiment of the present invention.

FIG. 7 illustrates an exemplary computer system that facilitates automatic generation of 3D masks, in accordance with an embodiment of the present invention. In this example, a computer system 700 includes a processor 702, a memory device 704, and a storage device 708. Furthermore, computer system 700 can be coupled to a display device 710, a keyboard 712, and a pointing device 714. Storage device 708 can store code for an operating system 716, a 3D mask generation system 718, and data 736.

3D mask generation system 718 can include instructions, which when executed by processor 702 can cause computer system 700 to perform methods and/or processes described in this disclosure. Specifically, 3D mask generation system 718 can include instructions for implementing a template mask library 720, a template matching module 722, landmark and boundary refinement module 724, boundary trim and landmark cut module 726, manual editing module 728, and library template comparison module 730.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disks, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described above can be included in hardware modules. For example, the modules described in FIG. 2 can be implemented in hardware, or a combination of hardware and software, and can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

The foregoing embodiments described herein have been presented for purposes of illustration and description only. They are not intended to be exhaustive or to limit the embodiments described herein to the forms disclosed. Accordingly, many modifications and variations will be apparent to practitioners skilled in the art. Additionally, the above disclosure is not intended to limit the embodiments described herein. The scope of the embodiments described herein is defined by the appended claims.

What is claimed is:

1. A method for generating a custom article to fit a target surface, the method comprising:
   receiving an input dataset that represents a 3D input mesh of the target surface;
   comparing the input dataset with a number of template cut meshes, wherein a respective template cut mesh includes one or more cutting paths that correspond to a boundary of the mesh;
   identifying a template cut mesh that produces a closest match with the input dataset;
   applying a global geometric transformation to the identified template cut mesh to warp the template cut mesh to conform to the input dataset;
   refining and projecting a set of boundary and landmark points from the template cut mesh to the input dataset to define one or more cutting paths for the input dataset; and
   applying the defined one or more cutting paths to the input dataset to produce a cut-and-trimmed mesh.

2. The method of claim 1, wherein the target surface is a human face.

3. The method of claim 1, wherein the custom article is a face mask.

4. The method of claim 1, further comprising using laser, scissors, or other physical cutting technology to selectively remove a material selected for the custom article based on the cut-and-trimmed mesh.

5. The method of claim 1, further comprising allowing manual editing of the defined cut paths prior to producing the custom article.

6. The method of claim 1, further comprising:
   determining that there is sufficient difference between the cut-and-trimmed mesh and the identified template cut mesh; and
   adding the cut-and-trimmed mesh to a library of template cut meshes.

7. The method of claim 1, wherein identifying the template cut mesh that produces the closest match with the input dataset comprises performing a global affine transformation between a respective template cut mesh and the input dataset.

8. The method of claim 1, wherein refining and projecting the boundary and landmark points from the template cut mesh to the input dataset comprises performing a locally varying affine transformation at each landmark point based on correspondence relationship between the template cut mesh and the input dataset as a result of the global geometric transformation.

9. The method of claim 1, wherein the one or more cutting paths further correspond to one or more openings within the boundary.

10. A computer system for generating a custom article to fit a target surface, the system comprising:
    a processor; and
    a storage device coupled to the processor and storing instructions, which when executed by the processor cause the processor to perform a method, wherein the method comprises:
    receiving an input dataset that represents a 3D input mesh of the target surface;
    comparing the input dataset with a number of template cut meshes, wherein a respective template cut mesh includes one or more cutting paths that correspond to a boundary of the mesh;
    identifying a template mesh that produces a closest match with the input dataset; and
    applying a global geometric transformation to the identified template cut mesh to warp the template cut mesh to conform to the input dataset;
    refining and projecting a set of boundary and landmark points from the template cut mesh to the input dataset to define one or more cutting paths for the input dataset; and
    applying the defined one or more cutting paths to the input dataset to produce a cut-and-trimmed mesh.

11. The computer system of claim 10, wherein the target surface is a human face.

12. The computer system of claim 10, wherein the custom article is a face mask.

13. The computer system of claim 10, wherein the method further comprises using laser, scissors, or other physical cutting technology to selectively remove a material selected for the custom article based on the cut-and-trimmed mesh.

14. The computer system of claim 10, wherein the method further comprises allowing manual editing of the defined cut paths prior to producing the custom article.

15. The computer system of claim 10, wherein the method further comprises:
    determining that there is sufficient difference between the cut-and-trimmed mesh and the identified template cut mesh; and
    adding the cut-and-trimmed mesh to a library of template cut meshes.

16. The computer system of claim 10, wherein identifying the template cut mesh that produces the closest match with the input dataset comprises performing a global affine transformation between a respective template cut mesh and the input dataset.

17. The computer system of claim 10, wherein refining and projecting the landmark points from the template cut mesh to the input dataset comprises performing a locally varying affine transformation at each landmark point based on correspondence relationship between the template cut mesh and the input dataset as a result of the global geometric transformation.

18. The computer system of claim 10, wherein the one or more cutting paths further correspond to one or more openings within the boundary.

19. A non-transitory computer-readable storage medium storing instructions which when executed by a computer system cause the computer system to perform a method for generating a custom article to fit a target surface, the method comprising:
    receiving an input dataset that represents a 3D input mesh of the target surface;
    comparing the input dataset with a number of template cut meshes, wherein a respective cut template cut mesh includes one or more cutting paths that corresponds to a boundary of the mesh;
    identifying a template cut mesh that produces a closest match with the input dataset;

applying a global geometric transformation to the identified template cut mesh to warp the template cut mesh to conform to the input dataset;

refining and projecting a set of boundary and landmark points from the template cut mesh to the input dataset to define one or more cutting paths for the input dataset; and applying the defined one or more cutting paths to the input dataset to produce a cut-and-trimmed mesh.

20. The non-transitory computer-readable storage medium of claim 19, wherein the custom article is a face mask.

\* \* \* \* \*